United States Patent
Boivin et al.

(10) Patent No.: US 12,403,328 B2
(45) Date of Patent: Sep. 2, 2025

(54) ENHANCED DOSE RATE/ULTRA-HIGH DOSE RATE RADIATION AND SPATIALLY FRACTIONED RADIATION THERAPY

(71) Applicant: Siemens Healthineers International AG, Palo Alto, CA (US)

(72) Inventors: Gael Boivin, Geneva (CH); Michael Folkerts, Costa Mesa, CA (US); Sophia Pfister, Redwood City, CA (US); Marta Vilalta, Belmont, CA (US); Vidhya Krishnamurthi, Los Altos, CA (US); Ricky Anupam Sharma, Lightwater (GB)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 413 days.

(21) Appl. No.: 17/950,005

(22) Filed: Sep. 21, 2022

(65) Prior Publication Data
US 2024/0091559 A1  Mar. 21, 2024

(51) Int. Cl.
*A61N 5/10* (2006.01)

(52) U.S. Cl.
CPC ......... *A61N 5/1038* (2013.01); *A61N 5/1065* (2013.01); *A61N 2005/1087* (2013.01)

(58) Field of Classification Search
CPC .......... A61N 2005/1087; A61N 5/1043; A61N 5/1001; A61N 5/103; A61N 5/1031;
(Continued)

(56) References Cited

U.S. PATENT DOCUMENTS

| | | |
|---|---|---|
| 2015/0087879 A1 | 3/2015 | Nelms |
| 2020/0282231 A1* | 9/2020 | Khuntia ............... A61N 5/1038 |
| 2021/0379404 A1 | 12/2021 | Basiri et al. |

FOREIGN PATENT DOCUMENTS

| | | |
|---|---|---|
| WO | WO-2020/018904 A1 | 1/2020 |
| WO | 2021099511 A1 | 5/2021 |

OTHER PUBLICATIONS

Ludovic De Marzi et al. Spatial fractionation of the dose in proton therapy: proton minibeam radiation therapy. Cancer/Radiothérapie, vol. 23, Issues 6-7. 2019, pp. 677-681,ISSN 1278-3218, <https://doi.org/10.1016/j.canrad.2019.08.001.> (https://www.sciencedirect.com/science/article/pii/S1278321819303063.
(Continued)

*Primary Examiner* — Don K Wong
(74) *Attorney, Agent, or Firm* — Harness, Dickey & Pierce, P.L.C.

(57) ABSTRACT

One or more new metrics are introduced into the treatment planning process. More specifically, a correcting factor/metric referred to herein as the critical/repair ratio index is introduced, and/or a correcting factor/metric referred to herein as the spatial periodicity of critical isodose value is introduced. By using these metrics, the expected sparing from the spatial distribution of dose is better accounted for in treatment modalities including spatially fractionated radiation therapy (SFRT) in general and SFRT with ultra-high dose rates in particular. According to a treatment planning strategy, the target can be covered by a Spread-Out Bragg Peak, to optimize and/or homogenize the dose distribution at the target level but still benefit from the sparing effect of SFRT at the healthy tissue level. Delivery techniques include a dynamic focusing technique and a magnetic
(Continued)

beam steering technique. Enhancing dose rate enables maximizing the peak-to-valley dose distribution with SFRT despite patient motion.

32 Claims, 7 Drawing Sheets

(58) Field of Classification Search
CPC .......... A61N 5/00; A61N 5/10; A61N 5/1038; A61N 5/1077; A61N 5/1048; A61N 2005/1057; A61N 5/1064; A61N 5/1065; A61N 5/1067; A61N 5/1068; A61N 5/1071

See application file for complete search history.

(56) References Cited

OTHER PUBLICATIONS

Tim Schneider et al. Advancing proton minibeam radiation therapy: magnetically focussed proton minibeams at a clinical centre. Sci Rep 10, 1384 (2020). https://doi.org/10.1038/s41598-020-58052-0.

Yolanda Prezado et al. Proton minibeam radiation therapy spares normal rat brain: Long-Term Clinical, Radiological and Histopathological Analysis. Sci Rep 7, 14403 (2017). https://doi.org/10.1038/S41598-017-14786-y.

Stefanie Girst et al. Proton Minibeam Radiation Therapy Reduces Side Effects in an In Vivo Mouse Ear Model, International Journal of Radiation Oncology, Biology, Physics, vol. 95, Issue 1, 234-241 (2015). http://dx.doi.org/10.1016/j.ijrobp.2015.10.020.

Yolanda Prezado et al. Tumor Control in RG2 Glioma-Bearing Rats: A Comparison Between Proton Minibeam Therapy Standard Proton Therapy, International Journal of Radiation Oncology*Biology*Physics, vol. 104, Issue 2, 2019, pp. 266-271, ISSN 0360-3016, https://doi.org/10.1016/j.ijrobp.2019.01.080. (https://www.sciencedirect.com/science/article/pii/S0360301619301713).

Yolanda Prezado et al. (2013), Proton-minibeam radiation therapy: A proof of concept. Med. Phys., 40: 031712.Å https://doi.org/10.1118/1.4791648.

* cited by examiner

ENHANCED DOSE RATE/ULTRA-HIGH DOSE RATE RADIATION AND SPATIALLY FRACTIONED RADIATION THERAPY

BACKGROUND

The use of radiation therapy to treat cancer is well known. Typically, radiation therapy involves directing a beam of radiation into a target in the body, such as a malignant tumor, a post-resection tumor bed, a site known to be at risk for tumor progression or a benign lesion, among others.

Radiation therapy using proton beams (proton therapy) has a significant advantage relative to the use of other types of beams. A proton beam reaches a depth in tissue that depends on the energy of the beam, and releases most of its energy (delivers most of its dose) at that depth. The region of a depth-dose curve where most of the energy is released is referred to as the Bragg peak of the beam.

Before a patient is treated with radiation, a treatment plan specific to that patient is developed. The treatment plan defines various aspects of the radiation therapy using simulations and optimizations that may be based on past experiences. In general, the purpose of the treatment plan is to deliver sufficient radiation to the unhealthy tissue while minimizing the exposure of surrounding healthy tissue to that radiation.

One radiation therapy technique is known as spatially fractionated radiation therapy (SFRT). In SFRT, multiple beams of radiation are directed into the target volume. The beams are spatially separated from each other; that is, they have different paths through the tissue along which they do not fully overlap with each other, creating a characteristic "peak and valley" dose distribution. Types of spatially separated beams include Grid lattice, minibeam and microbeams, beamlets, pencil beams (spot scanning beams), appropriately oriented and spaced. Minibeams are distinguishable from other types of GRID-SFRT techniques based on the distance separating the beams and their size. A minibeam may have a full width at half maximum (FVVHM) in the range of less than two millimeters (mm), while other types of SFRT beams are larger. For ease of discussion, the term "beam" is used herein in the most general way to include any size beam applied to SFRT.

SFRT can be delivered using several radiation treatment modalities, including Intensity Modulated Radiation Therapy (IMRT) and Intensity Modulated Particle Therapy (IMPT). In SFRT/IMRT, beams are beams are directed to the target using a collimator. Portions of a beam pass through openings (e.g., holes or slits) in the collimator, while the remaining portions of the beam are blocked or attenuated by the collimator. The openings in the collimator are located so that they are aligned with locations (e.g., spots) in the target volume that are specified in the treatment plan. In SFRT/IMPT, beams are focused into the target volume with a collimator and/or with scanning magnets in the nozzle of the treatment machine. In both cases, SFRT/IMPT controls the directions of relatively narrow beams that are directed into locations in the target volume that are specified in the treatment plan.

The advantage of SFRT is that it offers a better treatment tolerance profile for the healthy tissue as compared to a standard homogenous radiation therapy treatment. The biological mechanisms underlying this sparing effect are believed to correlate with the SFRT-specific successive high-dose peak to low-dose peak distribution. Because motion of the target and surrounding tissue during conventional dose delivery is expected to smooth out this dose distribution, motion is likely expected to reduce the overall advantage of SFRT.

Furthermore, conventional treatment planning systems do not adequately account for the spatial distribution of dose. For example, conventional dose-volume histogram (DVH) metrics that are used in the treatment planning process to evaluate the quality of proposed treatment plans do not account for the spatial distribution of dose.

SUMMARY

To address the problems described above, a new, dedicated metric that optimizes spatially fractionated radiation therapy (SFRT) treatment planning, including proton-SFRT treatment planning, is needed. Ideally, that metric should also account for the distribution of peaks that coincide with the paths of the incident spatially fractionated beams and valleys that coincide with the spacing between those beams, and should also be compatible with current dose-volume histogram (DVH) representations. Additionally, because the tolerance to proton-based SFRT is expected to be sensitive to motion, a motion mitigation strategy, compatible with the treatment planning system, is also needed.

Embodiments according to the present disclosure provide solutions that satisfy the above needs by introducing one or more new metrics into the treatment planning process. In embodiments, a correcting factor/metric referred to herein as the critical/repair ratio index (CRI) is introduced. In other embodiments, a correcting factor/metric referred to herein as the spatial periodicity of critical isodose value (SP-CIV) is introduced. In principle, these metrics enables planners and clinicians to better assess DVHs or even apply correcting factors to DVHs of SFRT (e.g., proton-SFRT) treatment plans.

The CRI is a metric that accounts for the area of a given isodose surface outside the target volume, in addition to the volume defined by that surface. More specifically, the CRI optimizes (e.g., maximizes) the surface area of the critically injured isodose volume during the treatment planning process.

The SP-CIV is a metric that, generally speaking, constrains the surface of the critically injured isodose volume so that the contour of that surface does not come within a certain distance of itself; that is, so that the contour does not fold back on itself. In an embodiment, a maximum SP-CIV and/or a minimum SP-CIV can be calculated as the maximum spatial periodicity and/or the minimum spatial periodicity of the contour given by that surface. In embodiments, the maximum SP-CIV cannot be greater than a first specified limit, and the minimum SP-CIV cannot be less than a second specified limit.

Embodiments according to the present disclosure can be used for radiation therapy/treatment modalities including but not limited to enhanced dose rate (EDR) radiation therapy (RT), ultra-high dose rate (UHDR) RT, and FLASH RT. EDR is defined as a dose rate ranging from one to 40 grays per second (Gy/s). UHDR is defined as a dose rate greater than 40 Gy/s. FLASH RT is a special case of UHDR RT, where in addition to the dose rate, the expected tolerance of the healthy tissue is greater than that expected from low dose rates, due to the so-called "FLASH effect." In particular, embodiments according to the present disclosure include combinations of SFRT (including SFRT with transmission proton beams; e.g., pencil beam scanning), EDR RT, UHDR RT, FLASH RT, and proton beams that have Spread-Out Bragg Peaks (SOBPs). As a consequence of those combinations, during treatment of a patient, a homogeneous curative dose can be delivered across the entire target volume by the spatially fractioned beams passing through healthy tissue. Another advantage of combinations of SFRT, EDR RT, UHDR RT, FLASH RT and proton beams (including transmission proton beams or proton beams with SOBPs) is that the effect of patient motion on the dose distribution pattern to the patient during treatment is eliminated or drastically reduced.

Also disclosed are techniques that can be used to deliver spatially fractionated beams in general, including transmission proton beams and proton beams that have SOBPs, to perform SFRT with EDR or UHDR or FLASH. Those techniques include the use of a collimator or a dynamic focusing technique and a magnetic beam steering technique.

These and other objects and advantages of embodiments according to the present invention will be recognized by one skilled in the art after having read the following detailed description, which are illustrated in the various drawing figures.

This summary is provided to introduce a selection of concepts that are further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments according to the present disclosure and, together with the detailed description, serve to explain the principles of the disclosure. The drawings are not necessarily drawn to scale.

DETAILED DESCRIPTION

Figure 1:
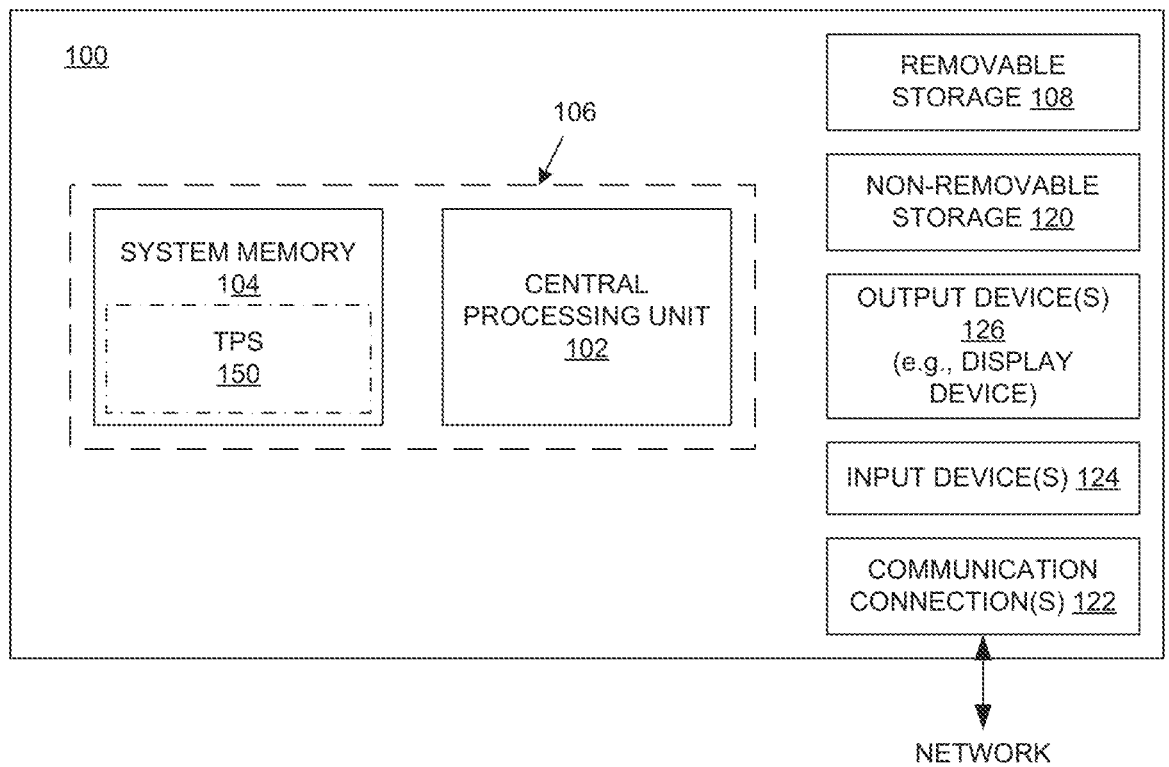
FIG. 1 is a block diagram of an example of a computer system upon which the embodiments described herein may be implemented.

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Some portions of the detailed descriptions that follow are presented in terms of procedures, logic blocks, processing, and other symbolic representations of operations on data bits within a computer memory. These descriptions and representations are the means used by those skilled in the data processing arts to most effectively convey the substance of their work to others skilled in the art. In the present application; a procedure, logic block, process, or the like, is conceived to be a self-consistent sequence of steps or instructions leading to a desired result. The steps are those utilizing physical manipulations of physical quantities. Usually, although not necessarily, these quantities take the form of electrical or magnetic signals capable of being stored, transferred, combined, compared, and otherwise manipulated in a computer system. It has proven convenient at times, principally for reasons of common usage, to refer to these signals as transactions, bits, values, elements, symbols, characters, samples, pixels, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present disclosure, discussions utilizing terms such as "accessing," "determining," "storing," "dividing," "optimizing," "minimizing," "maximizing," "producing," "generating," "evaluating," "calculating," "selecting," "graphically representing," or the like, refer to actions and processes (e.g., the flowchart of FIG. 11) of a computer system or similar electronic computing device or processor (e.g., the computer system 100 of FIG. 1). The computer system or similar electronic computing device manipulates and transforms data represented as physical (electronic) quantities within the computer system memories, registers or other such information storage, transmission or display devices.

Portions of the detailed description that follows are presented and discussed in terms of methods or processes. Although operations and sequencing thereof are disclosed herein, such operations and sequencing are examples only. Embodiments are well-suited to performing various other operations or variations of the operations described herein.

Embodiments described herein may be discussed in the general context of computer-executable instructions residing on some form of computer-readable storage medium, such as program modules, executed by one or more computers or other devices. By way of example, and not limitation, computer-readable storage media may comprise non-transitory computer storage media and communication media. Generally, program modules include routines, programs, objects, components, data structures, etc., that perform particular tasks or implement particular abstract data types. The functionality of the program modules may be combined or distributed as desired in various embodiments.

Computer storage media includes volatile and nonvolatile, removable and non-removable media implemented in any method or technology for storage of information such as computer-readable instructions, data structures, program modules or other data. Computer storage media includes, but is not limited to, random access memory, read only memory (ROM), electrically erasable programmable ROM (EEPROM), flash memory or other memory technology, compact disk ROM (CD-ROM), digital versatile disks (DVDs) or other optical or magnetic storage devices, or any other medium that can be used to store the desired information and that can be accessed to retrieve that information.

Communication media can embody computer-executable instructions, data structures, and program modules, and includes any information delivery media. By way of example, and not limitation, communication media includes wired media such as a wired network or direct-wired connection, and wireless media such as acoustic, radio frequency (RF), infrared and other wireless media. Combinations of any of the above can also be included within the scope of computer-readable media.

Nomenclature

The term "spatially separated beams" include GRID, lattice, beamlets, pencil beams (spot scanning beams), and minibeams, appropriately oriented and spaced. Minibeams are distinguishable from other types of beams based on their size. A minibeam may have a full width at half maximum (FVVHM) in the range of less than two millimeters (mm), while other types of beams are larger. For example, a pencil beam or beamlet may have a FWHM in the range of 4-5 mm. For ease of discussion, the term "beam" is used herein in the most general way to include any size beam, unless otherwise noted or apparent from the discussion.

The discussion to follow may include terms such as "dose," "dose rate," etc. Unless otherwise noted, a value is associated with each such term. For example, a dose has a value and can have different values. For simplicity, each of these terms means its value, unless otherwise noted or apparent from the discussion.

Introduction

FIG. 1 shows a block diagram of an example of a computer system 100 upon which the embodiments described herein may be implemented. In its most basic configuration, the system 100 includes at least one processing unit 102 and memory 104. This most basic configuration is illustrated in FIG. 1 by dashed line 106. The system 100 may also have additional features and/or functionality. For example, the system 100 may also include additional storage (removable and/or non-removable) including, but not limited to, magnetic or optical disks or tape. Such additional storage is illustrated in FIG. 1 by removable storage 108 and non-removable storage 120. The system 100 may also contain communications connection(s) 122 that allow the device to communicate with other devices, e.g., in a networked environment using logical connections to one or more remote computers.

The system 100 also includes input device(s) 124 such as a keyboard, mouse, pen, voice input device, touch input device, etc. Output device(s) 126 such as a display device, speakers, printer, etc., may also be included. A display device may be, for example, a cathode ray tube display, a light-emitting diode display, or a liquid crystal display.

In the example of FIG. 1, the memory 104 includes computer-readable instructions, data structures, program modules, and the like associated with a treatment planning system (TPS) 150, which may also be referred to as an optimizer. However, the TPS 150 may instead reside in any one of the computer storage media used by the computer system 100, or may be distributed over some combination of the computer storage media, or may be distributed over some combination of networked computers. The TPS 150 is used to generate and evaluate candidate (proposed) treatment plans and produce a final (optimized) treatment plan. A proposed radiation treatment plan is defined using the TPS 150, stored in a computer system memory, and accessed from that memory.

Figure 4:
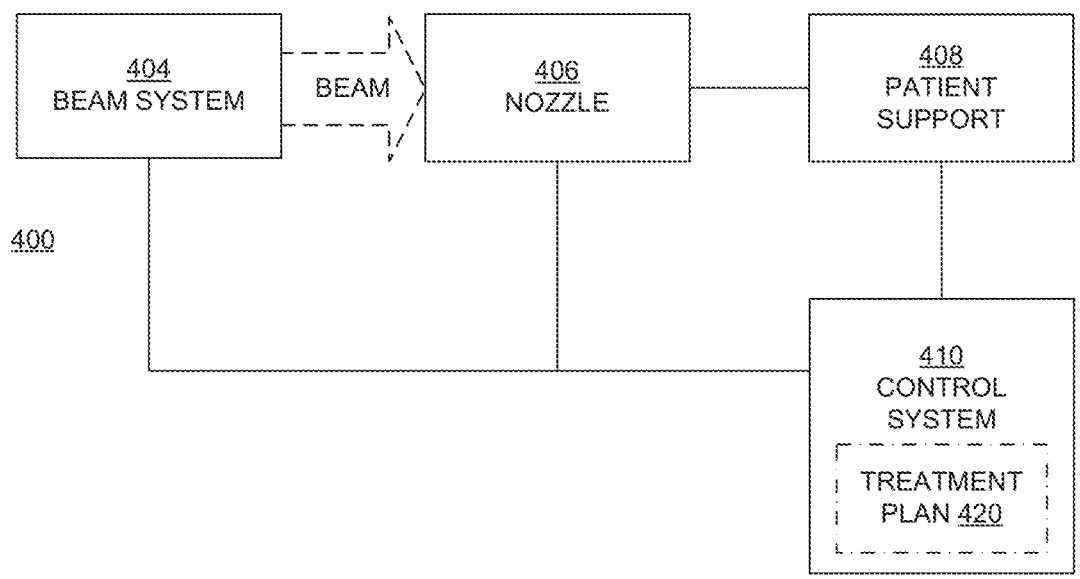
FIG. 4 is a block diagram showing selected components of a radiation therapy system upon which embodiments according to the present disclosure can be implemented.

To deliver the prescribed dose/dose rate of radiation, the radiation treatment plan can be converted (e.g., by the TPS 150) into machine parameters used to configure and control a treatment system (e.g., the system 400 of FIG. 4). Depending on the type of treatment, the machine parameters can include, but are not limited to, beam currents of charged particles, ions, or photon beam intensities, the number of charged particles, ions, or photons per time segment to be emitted by the accelerator, magnet currents, settings to achieve the prescribed energy of protons, ions, or photons at the target volume, and the measurement range of a dose monitor system.

During treatment, in an example embodiment, a beam enters a nozzle of a treatment machine, which may include one or more components that affect (e.g., decrease, modulate) the energy of the beam, to control the dose/dose rate delivered by the beam and/or to control the dose versus depth curve of the beam, depending on the type of beam. For example, for a beam that has a Bragg Peak, the nozzle can control the location of the Bragg Peak in the treatment target laterally to the beam axis.

Examples of Automated Radiation Treatment Planning Processes

The proposed radiation treatment plan includes values of parameters that can affect dose and/or dose rate, as well as other parameters. The parameters depend on the treatment modality. In embodiments of the present disclosure, the treatment modalities include spatially fractionated radiation therapy (SFRT), including intensity modulated radiation therapy (IMRT) and intensity modulated particle therapy (IMPT).

Depending on the treatment modality, the parameters may include, but are not limited to: beam shape; beam collimation; number and arrangement of spots; spot weights; beam weights; beam intensities or energies; beam directions; prescribed dose and prescribed dose rate; a number of irradiations of a target volume; a duration of each of the irradiations (irradiation times); and a dose deposited in each of the irradiations. The parameters may also include a period of time during which the irradiations are applied (e.g., a number of irradiations are applied over a period of time such as an hour, with each irradiation in the period of time separated from the next by another period of time; while a treatment session may be relatively long, individual beam delivery times may be less than, even much less than, a second) and an interval of time between each period of irradiations (e.g each hour-long period is separated from the next by a day).

The large number of parameters and their ranges of values can lead to an effectively infinite number of potential treatment plans, and therefore consistently and efficiently generating and evaluating high-quality treatment plans is beyond the capability of a human and relies on the use of a computing system, particularly considering the time constraints associated with the use of radiation therapy to treat ailments like cancer, as well as the large number of patients that are undergoing or need to undergo radiation therapy during any given time period.

Figure 2:
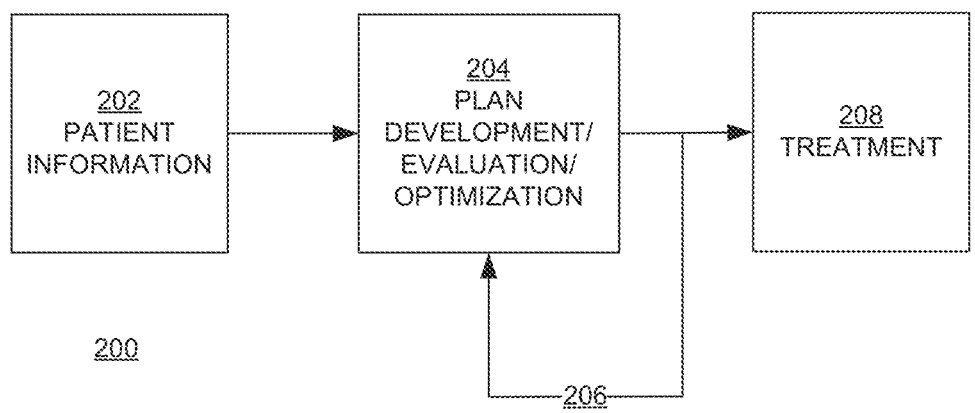
FIGS. 2 and 3 are block diagrams illustrating examples of an automated radiation therapy treatment planning process in embodiments according to the present disclosure.

FIG. 2 is a block diagram illustrating an example of an automated radiation therapy treatment planning process 200 in embodiments according to the present disclosure. The process 200, in whole or in part, may be implemented as a software program, hardware logic, or a combination thereof on/using the computer system 100 (FIG. 1).

In block 202 of FIG. 2, three-dimensional (3D) images of a patient are obtained, and organs and other structures in the patient (the patient geometry) can be segmented and contoured. In blocks 204 and 206, the information from block 202, and other information such as that mentioned above, are used to develop and evaluate a candidate treatment plan, as described further below in conjunction with FIG. 3.

In block 208, if the candidate treatment plan is satisfactory (e.g., it satisfies clinical goals), then the plan may be used for treatment of the patient. If not, then aspects of the treatment plan and/or of the clinical goals may be modified iteratively until a satisfactory plan is generated. The clinical goals may be expressed in terms of, for example, a set of quality metrics, such as target homogeneity, conformity to the treatment target, critical organ sparing, and the like, with respective target values for the quality metrics. A dose-volume histogram (DVH) or other types of graphical representations can be used to evaluate a treatment plan to determine whether the treatment plan satisfies clinical goals. For example, a treatment plan may be considered to be satisfactory if a DVH based on the plan satisfies a specified dose threshold for a specified percentage of the target volume.

Figure 3:
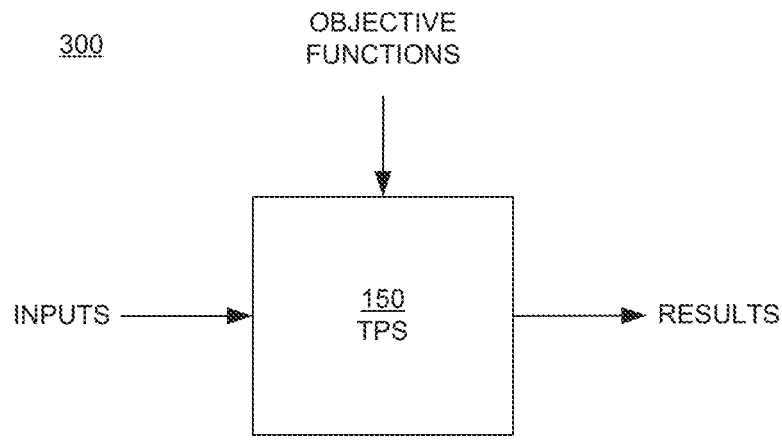

FIG. 3 is a block diagram illustrating an example of an automated radiation therapy treatment planning process 300 in embodiments according to the present disclosure. The process 300, in whole or in part, may be implemented as a software program, hardware logic, or a combination thereof on/using the computer system 100 (FIG. 1). The process 300 corresponds generally to blocks 204 and 206 of FIG. 2.

In the example of FIG. 3, the TPS 150 accesses or receives (e.g., from the memory 104 of FIG. 1) information that includes parameters such as those mentioned above. The TPS 150 can also access or receive information specific to the patient to be treated (e.g., patient geometry), including information that describes a treatment target (region of interest, ROI), which can include a planned target volume (PTV), gross tumor volume (GTV), clinical target volume (CTV), and organs-at-risk (OARs).

The TPS 150 also accesses or receives objective functions defined for the treatment of the patient. Objective functions are mathematical formulations of variables (parameters such as those mentioned above) that can have an effect on achieving specified clinical goals. More specifically, the objective functions are used to evaluate candidate radiation treatment plans, to determine whether or not the clinical goals that are specified for treatment of a patient are satisfied.

Example Treatment System

FIG. 4 is a block diagram showing selected components of a radiation therapy or treatment system 400 upon which embodiments according to the present invention can be implemented. In the example of FIG. 4, the system 400 includes a beam system 404 and a nozzle 406.

The beam system 404 generates and transports a beam. In embodiments, depending on the type of beam, the beam system 404 includes components that direct (e.g., bend, steer, focus, or guide) the beam in a direction toward and into a nozzle 406. The beam system 404 may also include components that are used to adjust (e.g., reduce or modulate) the beam energy entering the nozzle 406. The nozzle 406 is used to aim or direct the beam toward various locations or spots in a target volume within a patient supported on the patient support device 408 (e.g., a chair or table) in a treatment room. The nozzle 406 may be mounted on or a part of a gantry that can be moved relative to the patient support device 408, which may also be moveable. The nozzle 406 may also include components that direct the beam and/or adjust the beam energy. Additional information is provided below in the discussion of FIGS. 9, 10A, and 10B.

The control system 410 implements a prescribed or optimized or final radiation treatment plan 420 received from the TPS 150 (e.g., see FIG. 1). In embodiments, the control system 410 includes a computer system having a processor, memory, an input device (e.g., a keyboard), and perhaps a display, similar to the system 100 of FIG. 1. The control system 410 can receive data regarding operation of the system 400. The memory of the control system 410 stores the radiation treatment plan 420 that will be implemented using the system 400. Specifically, the memory of the control system 410 includes computer-readable instructions, data structures, program modules, and the like associated with the radiation treatment plan 420. The control system 410 can control parameters of the beam system 404, nozzle 406, and patient support device 408, including parameters such as the energy, intensity, direction, size, and/or shape of the beam, according to data it receives and according to the radiation treatment plan 420.

Correcting Factor in Treatment Planning

In general, embodiments disclosed herein model the expected sparing effect due to spatial distribution of dose in treatment modalities including, for example but not limited to, SFRT in general, and in particular proton-SFRT with enhanced dose rate (ESR), ultra-high dose rates (UHDRs), and proton beams with Spread-Out Bragg Peaks (SOBPs) or transmission proton beams (e.g., transmission-SFRT).

In embodiments according to the present disclosure, new correcting factors or metrics that may correlate with the sparing effect are introduced into the treatment planning process. In embodiments, a correcting factor/metric referred to herein as the critical/repair ratio index (CRI) is introduced. In embodiments, a correcting factor/metric referred to herein as the spatial periodicity of critical isodose value (SP-CIV) is introduced. CRI is discussed first further below, and SP-CIV is then discussed.

Embodiments according to the present disclosure can be used for radiation treatment or therapy (RT) modalities including but not limited to: CONVERT (Concurrent Once-Daily Versus Twice-Daily RT), enhanced dose rate (EDR) RT, UHDR RT, and FLASH RT. In general, for each of those modalities, the dose is delivered by a treatment system (e.g., the system 400 of FIG. 4) to a volume of tissue in less than one second. CONVERT delivers dose rates ranging between zero and one gray per second (Gy/s). EDR is defined as a dose rate ranging from one to 40 Gy/s. UHDR is defined as a dose rate greater than 40 Gy/s. FLASH RT is a special case of UHDR RT, where in addition to the dose rate, the expected tolerance of the healthy tissue is greater than that expected from low dose rates, due to the so-called "FLASH effect." In particular, embodiments according to the present disclosure include combinations of SFRT, EDR RT, UHDR RT, FLASH RT, and transmission proton beams or proton beams that have SOBPs.

Figure 5:
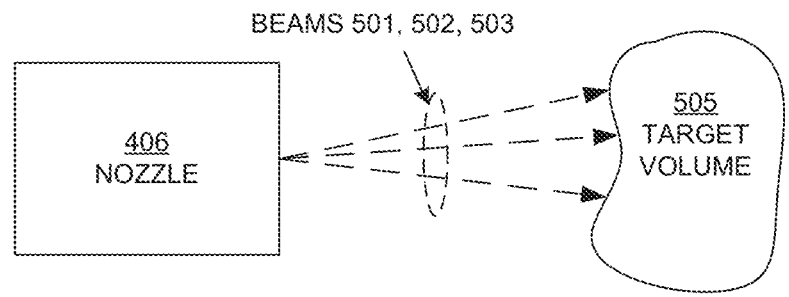
FIG. 5 illustrates an example of spatially fractionated beams in embodiments according to the present disclosure.

FIG. 5 shows three spatially fractionated proton beams 501, 502, and 503. In actual practice; there may be any number of such beams. The beams 501-503 are not necessarily being delivered at the same time; that is, they may or may not be temporally fractionated as well as spatially fractionated.

The beams 501-503 may be focused into the target volume 505 with a collimator, or they may be focused into the target volume with scanning magnets, or both, depending on the treatment modality. In embodiments, the respective ranges of the beams 501-503 are moderated so that their respective Bragg Peaks are within the target volume 505. In general, as will be seen from the discussions to follow, a homogeneous curative dose is delivered across the target volume 505 by the spatially fractioned beams 501-503.

Critical/Repair Ratio Index (CRI)

The CRI accounts for the area of a given isodose surface or contour outside the target volume, in addition to the volume defined by that surface. More specifically, the CRI optimizes (maximizes) the surface area of the critical isodose surface/contour during the treatment planning process. In principle, the metric enables planners and clinicians to better assess DVHs or even apply correcting factors to DVHs of SFRT (e.g., proton-SFRT) treatment plans. When using the metric with a correcting factor, DVHs can better account for the expected sparing from a spatial distribution of dose in the aforementioned treatment modalities. When using the metric without a correction factor, it allows discrimination between treatment plans with equivalently acceptable DVH distributions but different CRIs. According to the treatment planning strategy, the target volume can be covered by a SOBP or by transmission proton beams, to optimize and/or homogenize the dose distribution at the target level but still benefit from the sparing effect of SFRT at the healthy tissue level.

Figure 6A:
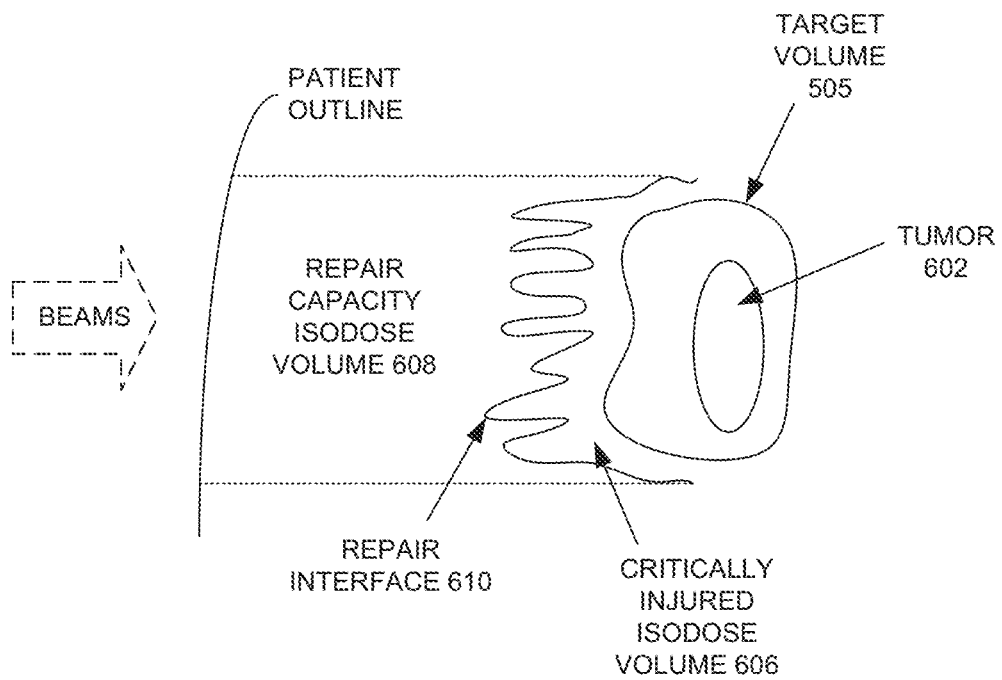
FIG. 6A is an illustration showing a cross-sectional view of a target volume in embodiments according to the present disclosure.

FIG. 6A is an illustration showing a cross-sectional view of a target volume 505 that includes a tumor 602, in embodiments according to the present disclosure. The target volume 505 may include tissue other than the tumor 602 (e.g.; tissue surrounding the tumor). In the example of FIG. 6A, spatially fractionated beams (like those in the example of FIG. 5) are directed toward and into the target volume 505 through other tissue in the patient from the direction shown. In the example of FIG. 6A, the other tissue includes a critically injured isodose volume 606 and a repair capacity isodose volume 608 that are traversed by the spatially fractioned beams. A repair interface 610 is at the interface of the critically injured isodose volume 606 and a repair capacity isodose volume 608.

In embodiments, the repair interface 610 is an isodose surface or contour (a surface that passes through points of equal dose in the tissue outside the target volume 505), and the critically injured isodose volume 606 is a volume defined by the repair interface. As such, the repair interface 610 represents the surface of the critically injured isodose volume 606. In an embodiment, the critically injured isodose volume 606 is instead a volume of the overlap between an organ-at-risk and an isodose surface (e.g., the repair interface 610).

In this example, the repair interface 610 is irregularly shaped or contoured as shown in FIG. 6A, with peaks that may coincide with the paths of the incident spatially fractionated beams, and valleys that coincide with the spacing between those beams. Conventional treatment planning systems and methods do not account for the irregular contour of the repair interface 610. In contrast, in embodiments according to the present disclosure, the irregular contour is accounted for using the aforementioned correcting factor (CRI) during treatment planning by the TPS 150 (e.g., FIG. 1).

In an embodiment, with reference still to FIG. 6A, an objective function to determine a value of CRI is defined as the amount of volume of the critically injured isodose volume 606 divided by the amount of surface area of the surface of the repair interface 610. A goal during treatment planning is to minimize the value of CRI by maximizing the surface area of the repair interface 610. In practice, as described further below, there may be several other objective functions in addition to CRI whose values are to be minimized in order to achieve an optimal final treatment plan.

Figure 7:
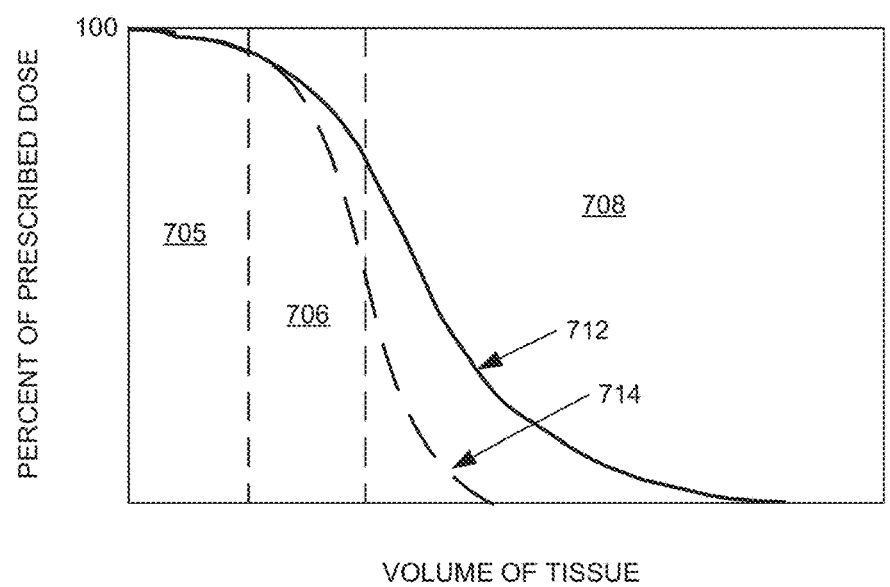
FIG. 7 is an example showing a comparison of a dose-volume histogram (DVH) determined conventionally for a candidate treatment plan to a DVH for the candidate treatment plan determined in embodiments according to the present disclosure.

Ideally, during planning and during the actual treatment, the dose would be delivered largely to the target volume 505, and the dose delivered to the critically injured isodose volume 606 and to the repair capacity isodose volume 608 would be minimized. FIG. 7 is an example showing a comparison of a DVH 712 determined conventionally for a candidate treatment plan (without CRI) to a DVH 714 for the candidate treatment plan determined according to the present disclosure (with CRI).

In the example of FIG. 7, with reference also to FIG. 6A, the region 705 corresponds to the target volume 505, the region 706 corresponds to the critically injured isodose volume 606, and the region 708 corresponds to the repair capacity isodose volume 608. As can be seen by the example, the DVH 714 is shifted relative to the DVH 712, which indicates that, by incorporating CRI into the treatment planning process, less of the volume of healthy tissue is projected to receive a dose.

Embodiments according to the present disclosure are not limited to the use of DVHs as just described. For treatment planning, the TPS 150 can graphically represent (display) the results of the CRI calculations in different ways to facilitate evaluation of the different candidate treatment plans by planners and clinicians or by (within) the TPS itself. In embodiments, a graphical representation includes a display of isodose values along the x-axis and values of the amounts of surface area of the repair interface 610 along the y-axis. As noted above, a goal during treatment planning is to minimize the value of CRI by maximizing the surface area of the repair interface 610, and so such a display can be useful for evaluating a candidate treatment plan.

Spatial Periodicity of Critical Isodose Value (SP-CIV)

The SP-CIV is a metric that, generally speaking, constrains the surface of the repair interface 610 so that it does not come within a certain distance of itself; that is, so that it does not fold back on itself. In a simple case, consider an example in which there are concentric rings of isodose values, in which case the SP-CIV is used to constrain the minimum value and/or the maximum value between such rings.

Figure 6B:
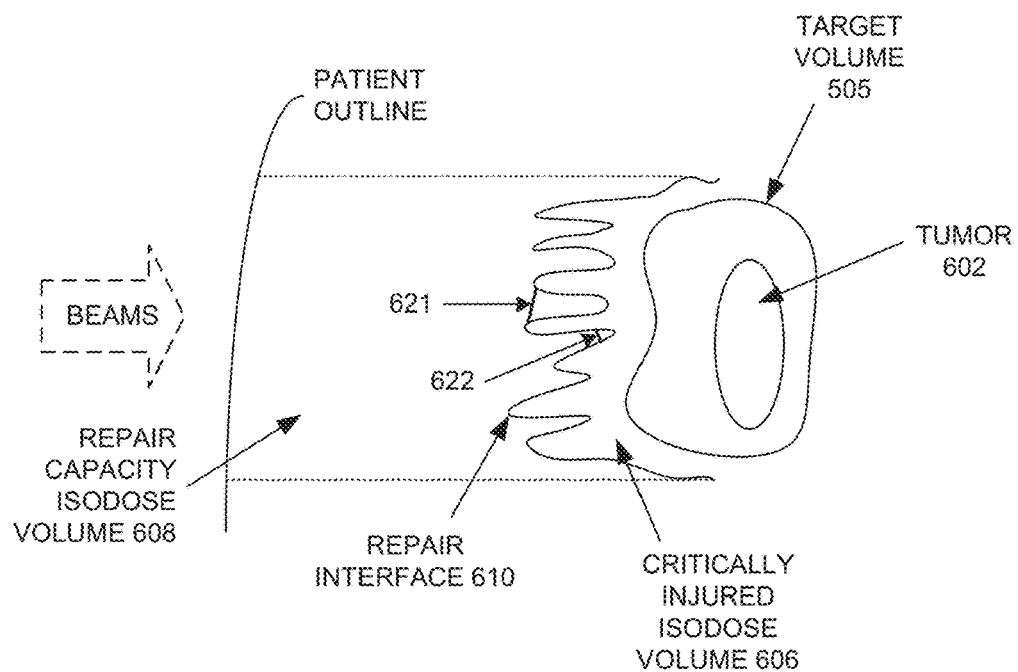
FIG. 6B is an illustration showing a cross-sectional view of a target volume in embodiments according to the present disclosure.

With reference to FIG. 6B, the line segment 621 represents the maximum distance between the same isodose value, and the line segment 622 represents the minimum distance between the same isodose value, on the repair interface 610 (each within some radius). That is, given a point on the contour of the repair interface 610, a search can be conducted (e.g., by the TPS 150) within some radius of that point to identify the maximum and minimum distances represented by the line segments 621 and 622, respectively. The SP-CIV can have a maximum value, or it can have a minimum value, or both its maximum and minimum values can be determined. In the example of FIG. 6B, the maximum value of SP-CIV is the length of the line segment 621, and the minimum value of SP-CIV is the length of the line segment 622. One or both of the maximum and minimum values of SP-CIV can be used by the TPS 150.

In an embodiment, the repair interface 610 can be modeled as a waveform having peaks and valleys, and the maximum SP-CIV and/or the minimum SP-CIV can be calculated with a Fourier transform that finds the maximum frequency (spatial periodicity) and/or the minimum frequency (spatial periodicity) of the dose distribution or contour given by the repair interface 610.

In embodiments, the maximum SP-CIV cannot be greater than a first specified limit. Similarly, in embodiments, the minimum SP-CIV cannot be less than a second specified limit. In general; the spatial periodicity of the repair interface 610 is constrained to a range between a minimum limit and a maximum limit.

Radiation Treatment/Therapy

As mentioned above, embodiments according to the present disclosure can be used for different RT modalities. Some embodiments according to the present disclosure combine SFRT, EDR or UHDR, and transmission proton beams or proton beams that have SOBPs. In those embodiments, the beams can be focused with either a collimator or using scanning magnets, or both, as previously described herein. As a consequence of that combination, during treatment of a patient, a homogeneous curative dose is delivered across the entire target volume by the spatially fractioned beams.

Figure 8:
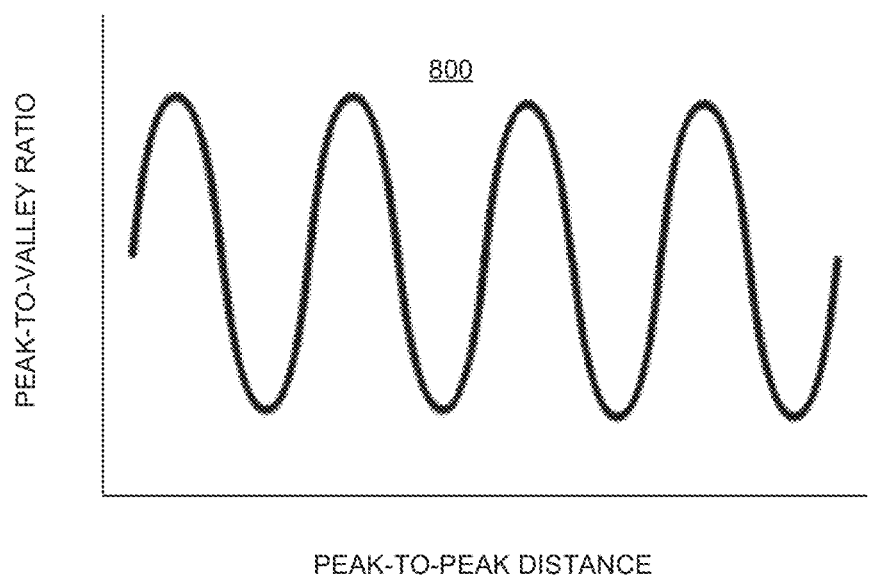
FIG. 8 illustrates characteristics of a proton beam, in embodiments according to the present disclosure.

Another advantage of combining SFRT, EDR or UHDR, and transmission proton beams or proton beams with SOBPs is that motion of the patient during treatment is mitigated. FIG. 8 illustrates a simplified pattern 800 of a proton beam as it would be measured by a detector at any point along a profile perpendicular to the beam axis, in embodiments according to the present disclosure. Even with motion, the pattern 800 exhibits a stable peak-to-valley ratio and a stable peak-to-peak distance, similar to a pattern that would be measured if there was no motion.

Spatial Fractionation Delivery Techniques

Various techniques can be used to deliver spatially fractionated beams in general and to perform SFRT with EDR or UHDR proton beams, including transmission proton beams or proton beams that have SOBPs in particular, to achieve a proton beam that has a stable peak-to-valley ratio and a stable peak-to-peak distance as illustrated in FIG. 8, and to deliver a homogeneous curative dose across the entire target volume.

Figure 9:
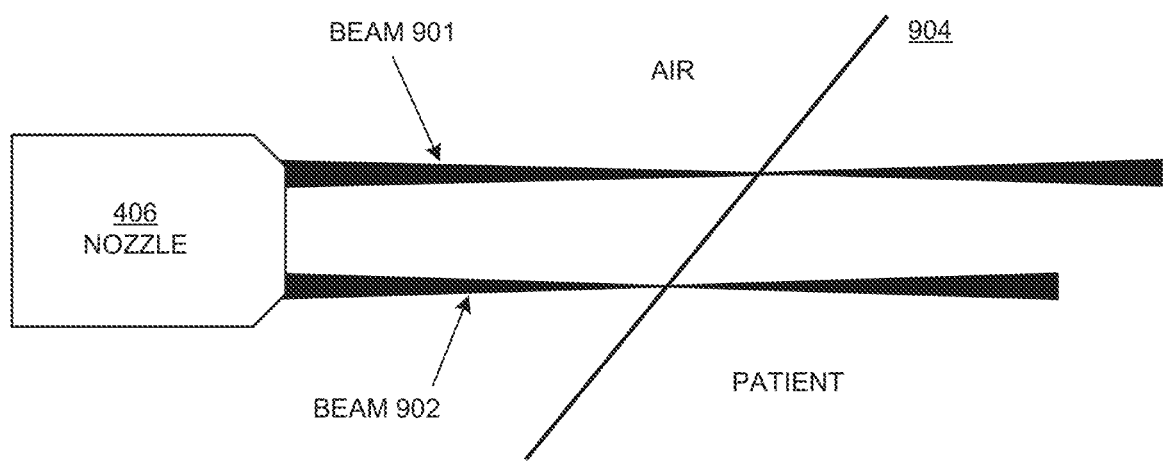
FIG. 9 illustrates an example of a dynamic spot focusing technique in embodiments according to the present disclosure.

FIG. 9 illustrates an example of a dynamic spot focusing technique in embodiments according to the present disclosure. In this example, two spatially fractionated beams 901 and 902 are shown as being emitted by a nozzle 406 of a treatment machine (e.g., the treatment system 400 of FIG. 4); however, the present disclosure is not so limited. The beams 901 and 902 may or may not be temporally fractionated as well as spatially fractionated.

In the dynamic spot focusing technique, the beams 901 and 902 of FIG. 9 are dynamically focused at the interface 904 between the patient and the surrounding environment (air). Dynamic focusing of one beam can be performed independently of any other beam. Instead of the interface 904, the focus points of the beams 901 and 902 can be at points that optimize (minimize) the value of the metric CRI while still achieving a prescribed or curative dose.

This dynamic focusing technique can be used to account for and mitigate patient motion during treatment. That is, the focus points of the beams 901 and 902 can be changed during treatment to compensate for any patient motion.

As illustrated in the example of FIG. 9, once a beam enters the patient, the width of the beam starts to broaden, and the beam continues to broaden with depth. To take advantage of the broadening aspect of the beams 901 and 902, it is desirable to focus the beams at the entrance point (e.g., the interface 904). This allows the beams 901 and 902 to overlap at the target volume, which facilitates delivery of a homogeneous curative dose across the entire target volume. However, it is also desirable for the beams 901 and 902 to be as narrow as possible outside of the target volume 505, to lessen the degree of exposure of healthy tissue to radiation. Focusing each of the beams 901 and 902 at the interface 904 facilitates achieving both of these goals.

Figure 10A:
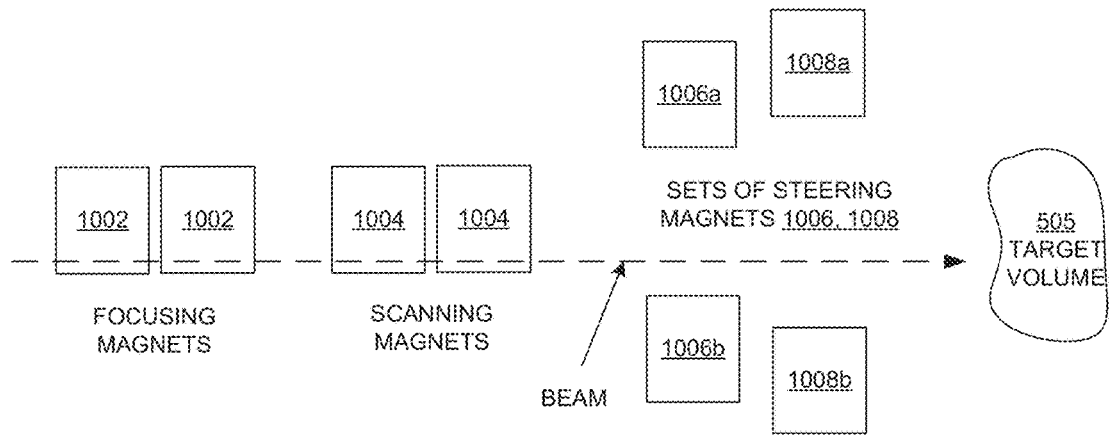
FIGS. 10A and 10B illustrate an example of a magnetic beam steering technique in embodiments according to the present disclosure.

FIG. 10A illustrates an example of a "dogleg" (e.g., double bending) magnetic beam steering technique in embodiments according to the present disclosure. In this example, the nozzle of a treatment machine (e.g., the nozzle 406 of the treatment system 400 of FIG. 4) includes a set of focusing magnets 1002 and a set of scanning magnets 1004. The nozzle 406 includes other components that are known in the art.

In embodiments according to the example of FIG. 10A, the treatment machine includes additional sets of magnets 1006 and 1008 that are coupled to (external to) the nozzle 406 or integrated into (internal to) the nozzle. In these embodiments, the first set of magnets 1006 includes a first pair of magnets 1006*a* and 1006*b*, and the second set of magnets 1008 includes a second pair of magnets 1008*a* and 1008*b*. In an embodiment, the magnets 1006*a* and 1006*b* are located on opposite sides of the beam path, facing each other along the beam path, and the magnets 1008*a* and 1008*b* are located on opposite sides of the beam path, facing each other along the beam path. In an embodiment, the sets of magnets 1006 and 1008 are positioned in the same plane. However, embodiments according to the present disclosure are not limited to the configurations just described. In general, the dogleg (e.g., double-bend) magnetic beam steering technique includes a set of magnets (e.g., the set 1006) along the x-axis of the beam path and another set (e.g., the set 1008) of magnets along the y-axis of the beam path. In an embodiment, the set of scanning magnets 1004 are not present in the treatment machine.

Figure 10B:
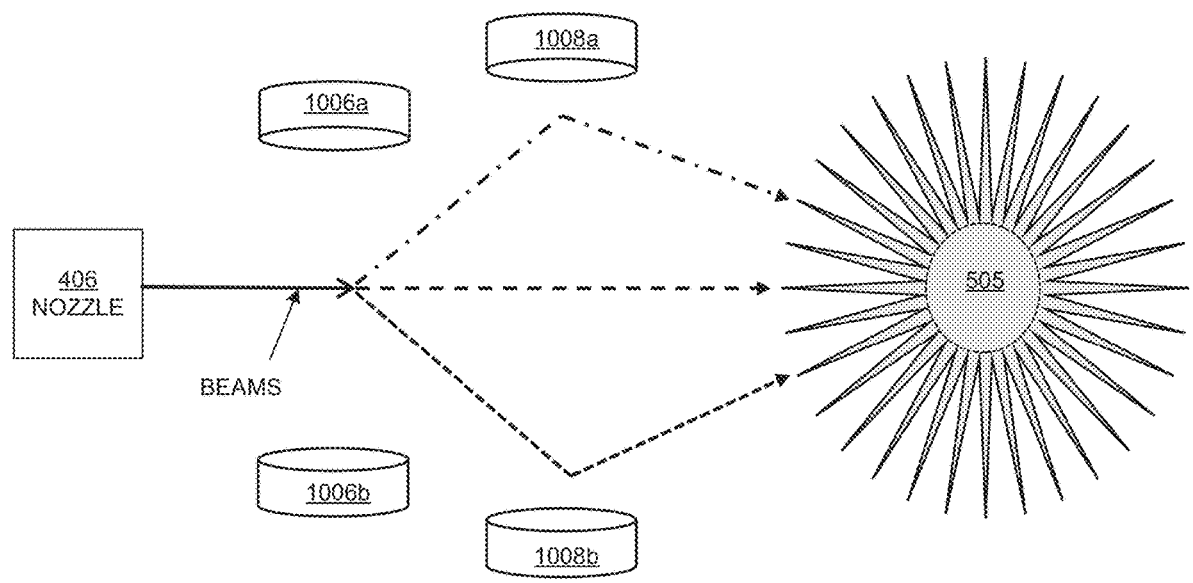

With reference to FIG. 10B, the first set of magnets 1006 steer a beam 1012 outward relative to its initial path, and the second set of magnets 1008 steer the beam back toward a location or spot in the target volume 505. The sets of magnets 1006 and 1008 can each be controlled in a complementary manner to direct beams to different spots in the target volume 505; that is, the angles of the beams can be controlled by the sets of magnets so that beams will enter the target volume at different spots and at different angles. The characteristics (e.g., field strength) of the sets of magnets 1006 and 1008 can be dynamically and quickly changed so that beams can be quickly delivered from different directions to multiple locations in the target volume 505.

The nozzle 406, including the sets of magnets 1006 and 1008, can also be moved relative to the target volume 505 (e.g., around the periphery of the patient or target volume)

to allow beams to be delivered from different directions. Generally speaking, the dogleg magnetic beam steering technique, in concert with the position of the nozzle 406, allows beams to be delivered to the target volume 505 from multiple different angles.

As described above, the beams will broaden as they travel through the patient, and as a result the beams will overlap in the target volume 505. Consequently, using this dogleg magnetic beam steering technique, the beams can deliver a homogeneous curative dose across the entire target volume 505 while creating a spatially fractionated dose in the healthy tissue.

Also, the beams may have SOBPs, and the ranges of the beams can be controlled in a known manner to control the depths (locations) of the SOBPs inside the target volume 505. This further facilitates delivery of a homogeneous dose across the entire target volume 505.

This dogleg magnetic beam steering technique can also be used to account for and mitigate patient motion during treatment. That is, the directions of the beams can be adjusted during treatment to compensate for any patient motion.

The dogleg magnetic beam steering technique is not limited to two sets of magnets. In some embodiments, the treatment machine includes a third set of magnets and a fourth set of magnets (not shown). The third set of magnets includes a third pair of magnets, and the fourth set of magnets includes a fourth pair of magnets. The third and fourth sets of magnets are positioned in the same plane, and that plane is orthogonal to the plane of the first and second sets of magnets 1006 and 1008. The third and fourth sets of magnets function similarly to the first and second sets of magnets 1006 and 1008, but steer the beams in different directions into the target volume 505.

In embodiments, both the dynamic focusing technique and the dogleg magnetic beam steering technique are utilized to focus and steer the beams.

Methods of Planning Treatment

Figure 11:
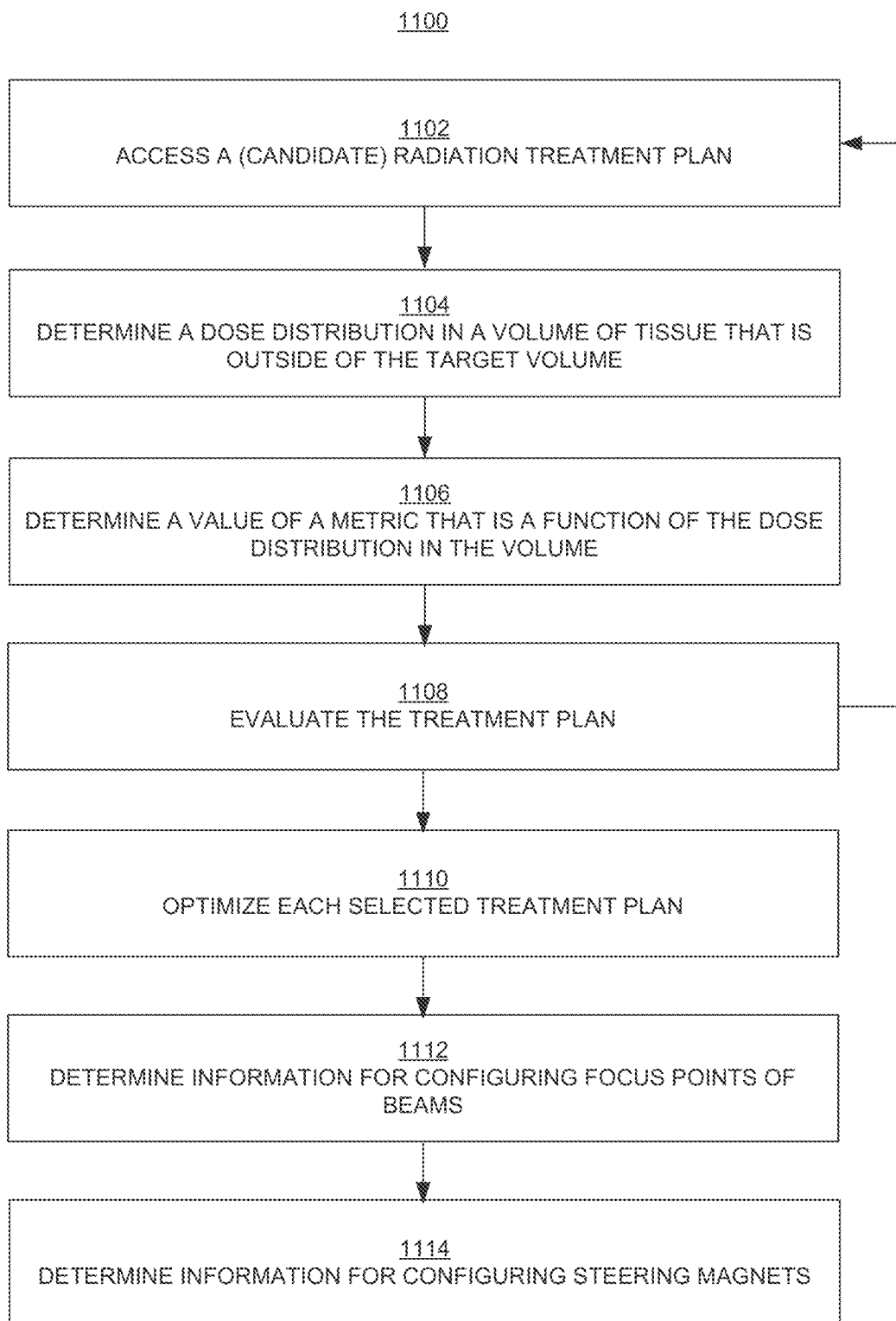
FIG. 11 is a flowchart of an example of a computer-implemented method for radiation treatment planning in embodiments according to the present disclosure.

FIG. 11 is a flowchart 1100 of an example of a computer-implemented method for radiation treatment planning in embodiments according to the present disclosure. The operations of the flowchart 1100 can be implemented as computer-executable instructions (e.g., the TPS 150 of FIG. 1) residing on some form of computer-readable storage medium (e.g., in memory of the computer system 100 of FIG. 1).

While the operations in the flowcharts of FIG. 11 are presented as occurring in series and in a certain order, the present invention is not so limited. The operations may be performed in a different order and/or in parallel, and they may also be performed in an iterative manner to obtain an optimal result.

As noted above, because of the different parameters that need to be considered, the range of values for those parameters, the interrelationship of those parameters, the need for treatment plans to be effective yet minimize risk to the patient, and the need to generate high-quality treatment plans quickly, the use of the treatment planning system 150 executing consistently on the computer system 100 (FIG. 1) for radiation treatment planning as disclosed herein is important.

In block 1102 of FIG. 11, a radiation treatment plan (e.g., a candidate treatment plan) is accessed from computer system memory. The treatment plan includes information describing a spatial distribution of radiation beams.

In block 1104, a distribution of dose in a volume of tissue (e.g., the critically injured isodose volume 606 of FIG. 6A) that is outside of the target volume and intersected by the radiation beams is determined.

In block 1106 of FIG. 11, a value of a metric that is a function of the distribution of the dose in the volume of the tissue is determined for the treatment plan.

In embodiments, the metric is CRI, and the value of the metric is determined using an objective function that is the value of the amount of a volume of the tissue (e.g., the volume of the critically injured isodose volume 606 of FIG. 6A) divided by the value of the amount of a surface area of that volume (the surface area of the repair interface 610). In embodiments, the value for the amount of the surface area is the maximum value for the isodose surface delineating the volume of the tissue.

In embodiments, the metric is SP-CIV, and the value of the metric determined using an objective function that calculates a spatial periodicity of the isodose surface, and the spatial periodicity is constrained by at least one of a maximum value and a minimum value.

In block 1108 of FIG. 11, the radiation treatment plan is evaluated to determine whether the plan satisfies clinical goals for the radiation treatment.

The operations of blocks 1102-1108 can be repeated for any practical number of treatment plans, to identify and select a set of one or more candidate treatment plans that satisfy the clinical goals. In block 1110, each selected treatment plan can be evaluated (optimized) to determine a final (optimized) treatment plan that can be used to treat the patient.

In embodiments, optimizing a treatment plan includes determining the minimum value of a total objective (e.g., cost) function that includes a summation of objective functions for that plan, including an objective function based on CRI and/or SP-CIV. For example, a planner defines a set of quality metrics. For planning, the metrics are defined such that a smaller value is preferred over a larger value. The planner also defines a relative priority or weight for each of the quality metrics. The task of developing an optimal plan is then formulated as a quadratic objective function. The optimal plan is determined by minimizing the objective function.

In practice the clinical goals may conflict with each other, in the sense that not all of the clinical goals can be satisfied by any particular treatment plan. Where clinical goals conflict, multicriteria optimization (MCO) can be used to optimize the treatment plan. Some or all of the parameter values for each candidate radiation treatment plan can be iteratively adjusted to determine a final set of parameter values (e.g., a spatial distribution of radiation beams, beam weights, intensities or energies, and directions, as well as other parameters previously described herein) for each plan that results in a plan that satisfies the objectives (clinical goals) for treatment of the patient and minimizes the total objective function for that plan. For instance, a dose prediction model (e.g., an element of the TPS 150 of FIG. 1) can be used to generate alternative outcomes for various combinations of the adjustable parameters, and the objective function can be computed for various alternative outcomes until a minimum or satisfactory value of the objective function is found.

In embodiments, a candidate treatment plan that yields a total objective function value closest to the minimum (relative to other proposed plans) can be identified as an optimized treatment plan. Information about the optimized treatment plan can be presented to the user (e.g., in a display that includes data about dose distribution, such as a DVH for various volumes of interest). A planner can iterate on the planning process, e.g., by adjusting weights in the total objective function and/or by adjusting the clinical goals. Once a final optimized treatment plan is determined, adjustable treatment machine parameters corresponding to the final optimized treatment plan can be provided in machine-readable form to the radiation treatment system, which can then be operated in accordance with the plan to deliver radiation treatment to a patient.

In another embodiment, the optimization algorithm selects a final optimized treatment plan as the plan, from among the different candidate plans, that has the best (e.g., minimum) CRI value for a given range of isodoses, and/or that has a SP-CIV that best satisfies the minimum and/or maximum limits on that metric.

In block 1112, in some embodiments, information for configuring focus points for the radiation beams are determined, where the focus points are at an interface between air and the patient.

In block 1114, in some embodiments, information for configuring magnets that control directions of the radiation beams is determined, where the magnets include: a first set of magnets that steer the radiation beams outward from their initial paths, and a second set of magnets downstream of the first set and that steer the radiation beams toward locations in the target volume.

The methodologies disclosed herein may also be useful for stereotactic radiosurgery as well as stereotactic body radiotherapy with single or multiple metastases.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer system, comprising:
a processor; and
memory coupled to the processor and comprising instructions that, when executed, cause the processor to perform a method used for planning radiation treatment of a target volume in a patient, the method comprising:
accessing, from the memory, a first candidate radiation treatment plan comprising information describing a spatial distribution of radiation beams;
determining a distribution of dose in a volume of tissue that is outside of the target volume and intersected by the radiation beams;
determining a value of a metric that is a function of the distribution of the dose in the volume of the tissue; and
evaluating the first candidate radiation treatment plan using the value of the metric.

2. The computer system of claim 1, wherein said determining the value of the metric comprises:
determining a value for an amount of the volume of the tissue, wherein the volume of tissue is delineated by an isodose surface; and
determining a value for an amount of a surface area of the volume of the tissue;
wherein the value of the metric is the value of the amount of the volume of the tissue divided by the value of the amount of the surface area.

3. The computer system of claim 1, wherein said determining the value of the metric comprises determining a spatial periodicity of an isodose surface that delineates the volume of tissue, wherein the spatial periodicity of the isodose surface is constrained by at least one of a maximum value and a minimum value.

4. The computer system of claim 1, further comprising maximizing a value for an amount of surface area of an isodose surface delineating the volume of the tissue.

5. The computer system of claim 1, wherein said evaluating further comprises:
determining a respective value of the metric for each candidate radiation treatment plan of a plurality of candidate radiation treatment plans including the first candidate radiation treatment plan; and
selecting a radiation treatment plan, from the plurality of candidate radiation treatment plans, having a minimum said respective value of the metric.

6. The computer system of claim 1, wherein the volume of the tissue is a volume selected from the group consisting of: a volume between an isodose surface and the target volume, and a volume of overlap between an organ-at-risk and an isodose surface.

7. The computer system of claim 1, wherein the method further comprises determining a dose-volume histogram based on the distribution of the dose in the volume of the tissue and a distribution of dose in the target volume.

8. The computer system of claim 1, wherein said evaluating produces a final radiation treatment plan that is configured to provide a curative dose across the target volume.

9. The computer system of claim 1, wherein the radiation beams are proton beams, and wherein the dose is delivered by a treatment system to the volume of the tissue in less than one second.

10. The computer system of claim 1, wherein the method further comprises determining information for configuring focus points for the radiation beams, and wherein the focus points are at points selected from the group consisting of: points at an interface between air and the patient, and points that optimize the value of the metric and provide a curative dose across the target volume.

11. The computer system of claim 1, wherein the method further comprises determining information for configuring a plurality of magnets that controls directions of the radiation beams, wherein the plurality of magnets comprises a first set of magnets that steer the radiation beams outward from their initial paths, and wherein the plurality of magnets further comprises a second set of magnets downstream of the first set and that steer the radiation beams toward locations in the target volume.

12. A system, comprising:
a beam system that generates radiation beams;
a nozzle coupled to the beam system and that directs the radiation beams to a target volume; and
a control system coupled to the beam system and to the nozzle, the control system comprising a computer system comprising a processor and a memory coupled to the processor;
wherein the memory stores a radiation treatment plan comprising information describing a spatial distribution of the radiation beams and a dose-volume histogram (DVH) for the target volume and for a volume of tissue that is outside of the target volume and intersected by the radiation beams, wherein the DVH is based on a value of a metric that is a function of the spatial distribution of a dose in the volume of the tissue; and
wherein the beam system and the nozzle are controlled by the control system according to the radiation treatment plan to deliver the dose to the target volume.

13. The system of claim 12, wherein the value of the metric is equal to an amount of the volume of the tissue divided by a value of an amount of a surface area of the volume of the tissue, wherein the volume of tissue is delineated by an isodose surface.

14. The system of claim 12, wherein the metric is a spatial periodicity of an isodose surface that delineates the volume of tissue, wherein the value of the metric is constrained by at least one of a maximum value and a minimum value.

15. The system of claim 12, wherein the volume of the tissue is a volume selected from the group consisting of: a volume between an isodose surface and the target volume, and a volume of overlap between an organ-at-risk and an isodose surface.

16. The system of claim 12, wherein the dose delivered to the target volume is a curative dose across the target volume.

17. The system of claim 12, wherein the radiation beams are proton beams, and wherein the dose is delivered by a treatment system to the volume of the tissue in less than one second.

18. The system of claim 12, wherein the radiation treatment plan further comprises information for configuring focus points for the beams, and wherein the focus points are points selected from the group consisting of: points at an interface between air and a patient, and points that optimize the value of the metric and provide a curative dose across the target volume.

19. The system of claim 12, further comprising a plurality of magnets that controls directions of the radiation beams, wherein the plurality of magnets comprises a first set of magnets that steer the beams outward from their initial paths, wherein the plurality of magnets further comprises a second set of magnets downstream of the first set and that steer the radiation beams toward locations in the target volume, and wherein the radiation treatment plan further comprises information for configuring the plurality of magnets.

20. A computer-implemented method used for planning radiation treatment of a target volume in a patient, the method comprising:
    accessing, from a computer system memory, a candidate radiation treatment plan comprising information describing a spatial distribution of radiation beams;
    determining a distribution of dose in a volume of tissue that is outside of the target volume and intersected by the radiation beams;
    determining a value of a metric that is a function of surface area of an isodose surface of the volume of tissue; and
    determining whether the candidate radiation treatment plan satisfies clinical goals for the radiation treatment using the value of the metric.

21. The computer-implemented method of claim 20, wherein said determining the value of the metric comprises:
    determining a value for an amount of the volume of the tissue, wherein the volume of tissue is delineated by the isodose surface; and
    determining a value for an amount of the surface area; wherein the value of the metric is the value of the amount of the volume of the tissue divided by the value of the amount of the surface area.

22. The computer-implemented method of claim 20, wherein said determining the value of the metric comprises determining a spatial periodicity of an isodose surface that delineates the volume of tissue, wherein the value of the metric is constrained by at least one of a maximum value and a minimum value.

23. The computer-implemented method of claim 20, further comprising determining a dose-volume histogram based on the distribution of the dose in the volume of the tissue and a distribution of dose in the target volume.

24. The computer-implemented method of claim 20, wherein the volume of the tissue is a volume selected from the group consisting of: a volume between the isodose surface and the target volume, and a volume of overlap between an organ-at-risk and the Isodose surface.

25. The computer-implemented method of claim 20, wherein the radiation beams are proton beams, and wherein the dose Is delivered by a treatment system to the volume of the tissue In less than one second.

26. The computer-implemented method of claim 20, further comprising determining information for configuring focus points for the radiation beams, wherein the focus points are points selected from the group consisting of: points at an interface between air and the patient, and points that optimize the value of the metric and provide a curative dose across the target volume.

27. The computer-implemented method of claim 20, further comprising determining information for configuring a plurality of magnets that controls directions of the radiation beams, wherein the plurality of magnets comprises a first set of magnets that steer the radiation beams outward from their initial paths, and wherein the plurality of magnets further comprises a second set of magnets downstream of the first set and that steer the radiation beams toward locations in the target volume.

28. A system, comprising:
    a beam system that generates radiation beams, wherein the radiation beams are proton beams;
    a plurality of magnets that controls directions of the radiation beams relative to a target volume; and
    a control system coupled to the beam system and to a nozzle, the control system comprising a computer system comprising a processor and a memory coupled to the processor;
    wherein the memory stores a radiation treatment plan that is based on a metric that maximizes a surface area of an isodose surface that is outside the target volume; and
    wherein the beam system and the nozzle are controlled by the control system according to the radiation treatment plan to deliver a dose to the target volume in less than one second.

29. The system of claim 28, wherein a value of the metric is equal to an amount of a volume of tissue that is outside of the target volume and intersected by the radiation beams, divided by a value of an amount of the surface area, and wherein the volume of tissue is delineated by the isodose surface.

30. The system of claim 29, wherein the volume of the tissue is a volume selected from the group consisting of: a volume between the isodose surface and the target volume, and a volume of overlap between an organ-at-risk and the isodose surface.

31. The system of claim 28, wherein a spatial periodicity of the isodose surface is constrained by at least one of a maximum value and a minimum value.

32. The system of claim 28, wherein the plurality of magnets comprises a first set of magnets that steer the radiation beams outward from their initial paths, wherein the plurality of magnets further comprises a second set of magnets downstream of the first set and that steer the beams toward locations in the target volume.

* * * * *